United States Patent [19]

Glassman

[11] 4,200,101
[45] Apr. 29, 1980

[54] CATAMENIAL TAMPON

[76] Inventor: Jacob A. Glassman, 1680 Meridian Ave., Miami Beach, Fla. 33139

[21] Appl. No.: 786,290

[22] Filed: Apr. 11, 1977

[51] Int. Cl.$^2$ ............................................. A61F 13/20
[52] U.S. Cl. ..................................... 128/285; 128/270
[58] Field of Search .................. 128/285, 270; 28/120

[56] References Cited

U.S. PATENT DOCUMENTS

| 2,134,930 | 11/1938 | Reynolds | 128/285 |
| 2,884,925 | 5/1959 | Meynier, Jr. | 128/285 X |
| 2,905,175 | 9/1959 | Schwartz | 128/270 |
| 3,085,574 | 4/1963 | Pensica | 128/285 X |
| 3,335,726 | 8/1967 | Maranto | 128/270 |
| 3,420,234 | 1/1969 | Phelps | 128/285 |
| 3,515,138 | 6/1970 | Hochstrasser et al. | 128/270 |

FOREIGN PATENT DOCUMENTS

| 808851 | 3/1969 | Canada | 128/285 |
| 2340084 | 5/1976 | France | 128/285 |

Primary Examiner—Stephen C. Pellegrino
Attorney, Agent, or Firm—Elmer L. Zwickel

[57] ABSTRACT

A catamenial tampon shaped to be fitted easily into the vagina and be withdrawn therefrom without discomfort notwithstanding deep radial expansion of it's insert end prior to insertion. The disclosure is also concerned with the method of fabricating one embodiment thereof.

8 Claims, 23 Drawing Figures

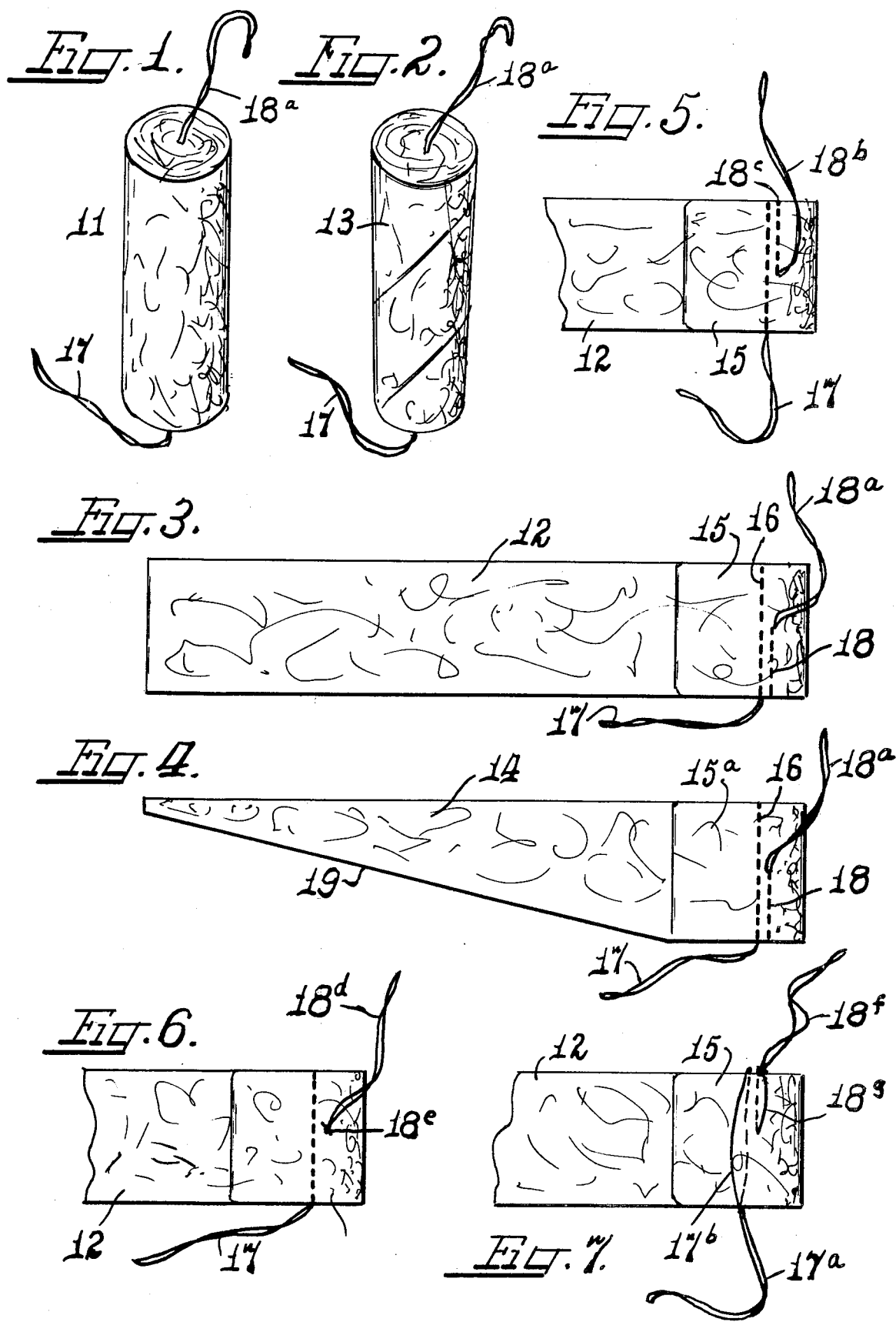

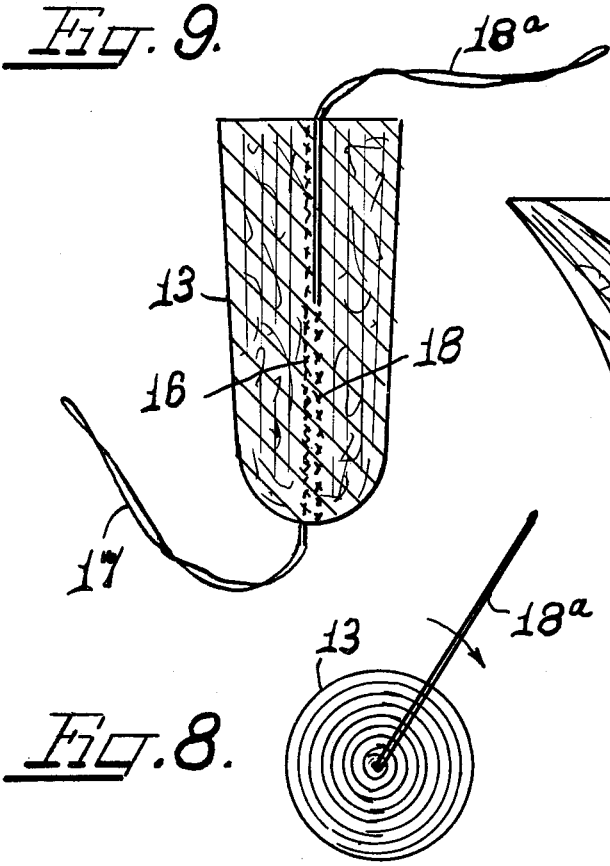
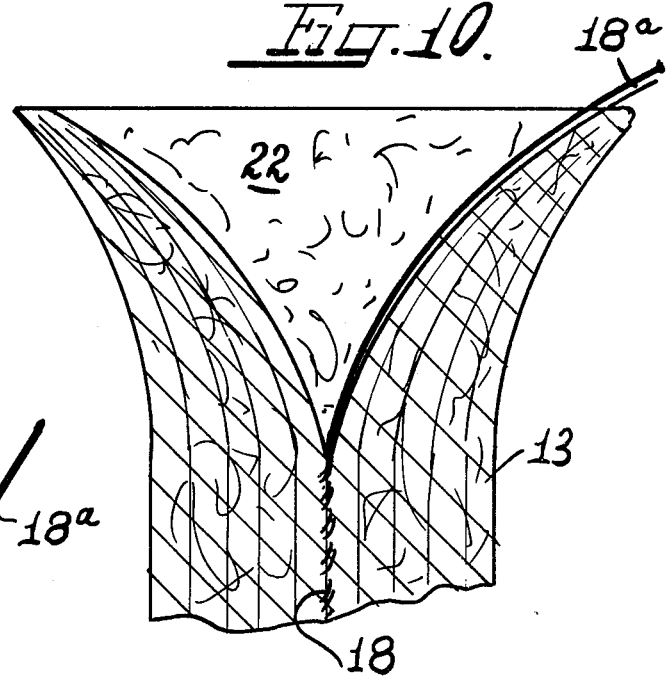
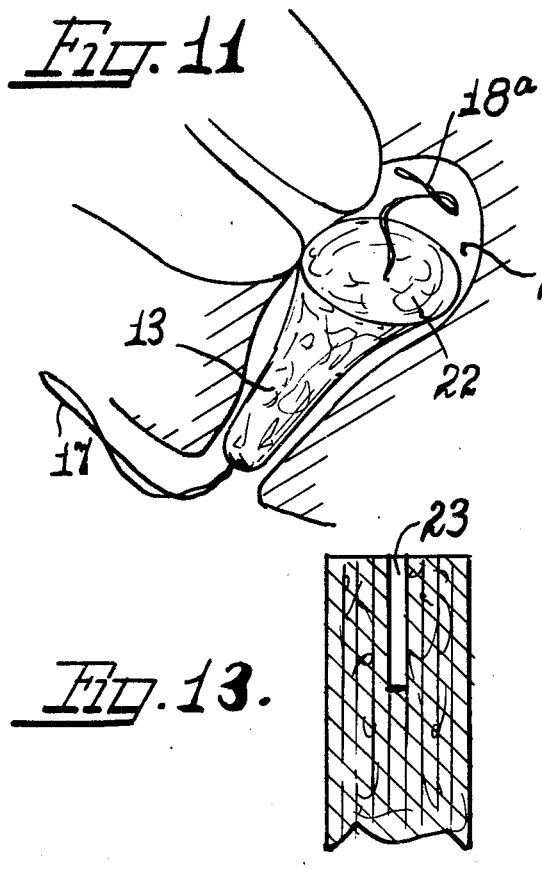
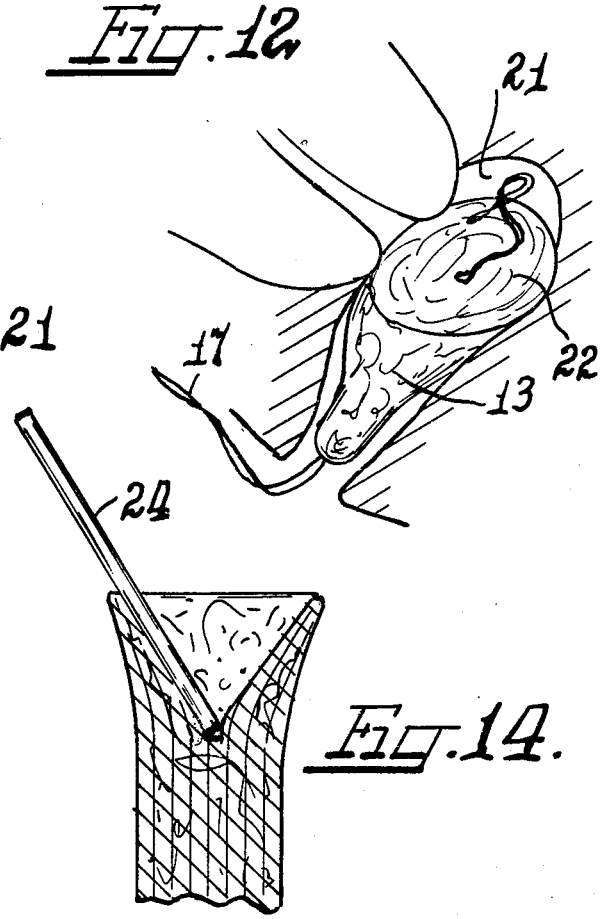

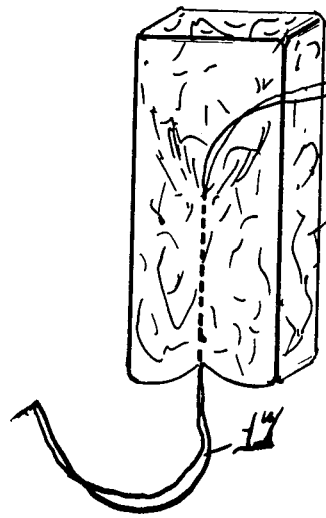
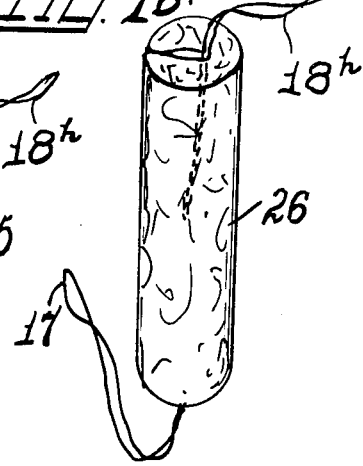
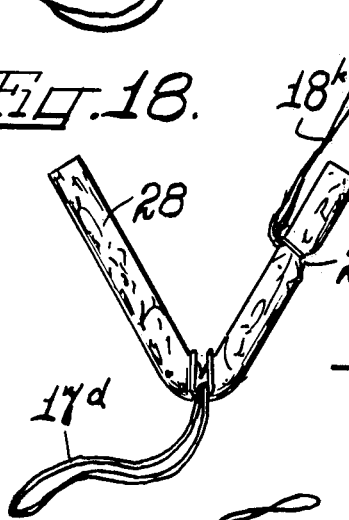
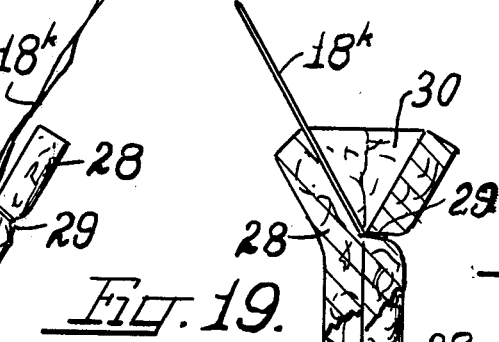
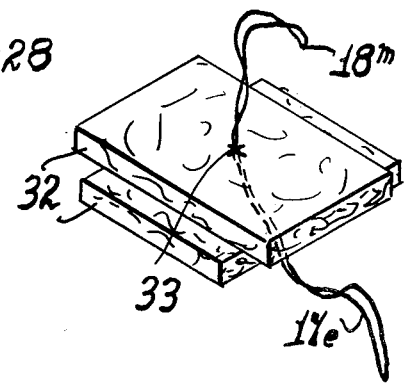
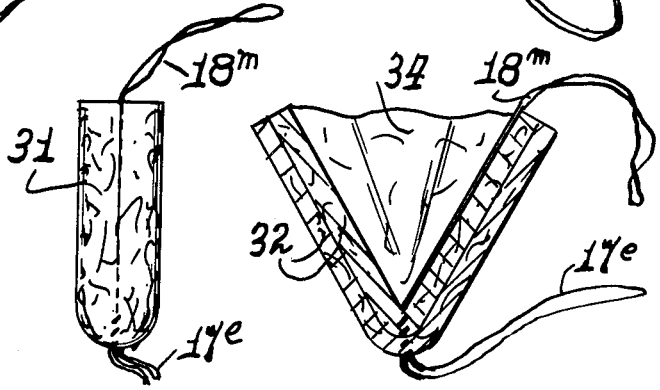
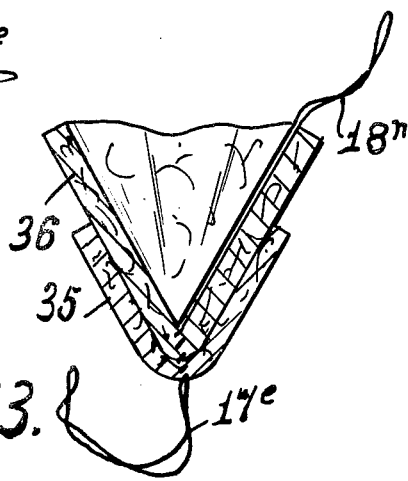

CATAMENIAL TAMPON

The invention relates to improvements in catamenial tampons and is particularly concerned with improvements in the tampon structures shown and described in my co-pending application Ser. No. 764,009, filed Jan. 25, 1977, now abandoned. In the aforesaid pending application the tampon was provided with a spread-out string anchored to the tampon closely adjacent to its insert end adapted to be manipulated to cause radial expansion of the insert end of the tampon in such manner as to develop a shallow recess or cavity intended for the reception of medication, etc. The cavity or recess thus provided has limited capacity, consequently, in instances requiring massive medication, it's effectiveness is limited.

The present disclosure embodies a structure that has novel means to cause radial expansion or "flowering" of a much larger portion of the tampon; i.e.: approximately one-half it's length, so as to create a recess or cavity of greater capacity than heretofore possible. In other respects the tampons disclosed herein are substantially like those disclosed in the aforesaid application.

The present disclosure involves the formation of a compress cylindrical tampon or a compressed frusto-conical shaped tampon having it's greater diameter at it's insert end. The latter type is advantageous because it will resist displacement in the vagina while dry and, upon swelling with absorption of fluids, it will conform substantially to the natural circumference and taper of the vagina wall and cervix and fit snugly in the vaginal contour. In order to adapt either type of tampon to the reception of medication, be it a tablet, a capsule, a pill, a powder, or a cream, radial expansion of the insert is effected to generate a cavity or recess in said insert end. This is made possible by providing the insert end with a string or other element that is grasped and moved in a circular path about the axis of the tampon so as to cause the insert end to be expanded or "flowered" thus creating the aforesaid recess or cavity. In the present disclosure except in FIGS. 13–14, the string is free of a substantial portion of the tampon body so that when moved circumferentially to generate the recess or cavity, it causes a substantial portion of the insert end of the tampon to be "flowered" and thereby generate a cavity or recess of considerable depth. Of course, by varying the point of attachment of the string, the depth of the cavity can be varied.

Because the diameter of the expanded insert end of the tampon is greater than the tail end, the tampon can be and preferably is easily and effectively inserted into the vagina by a doctor or gynecologist. Professional insertion is highly preferable in instances when medication is required. Now, when the tampon is properly inserted toward the roof of the vagina and/or to the cervix level and upper vaginal canal, all portions can be effectively treated locally with medication. Also, if desired, the tail end of the tampon can be "flowered" outwardly by similar manipulation of the conventional pull string normally on the tampon.

It is therefore an object of the invention to provide a catamenial tampon with novel means to facilitate the generation of a recess or cavity of variable depth in its insert end.

Another object is to provide such a catamenial tampon with structural characteristics that adapt it to substantially fill the vagina into which it is inserted and to be easily withdrawn.

Other objects and advantages of the invention will become apparent upon reference to the following description and accompanying drawings.

IN THE DRAWINGS

FIG. 1 is a perspective view of a cylindrical tampon embodying features of the invention.

FIG. 2 is a similar view of a frusto-conical tampon embodying features of the invention.

FIG. 3 is a view of a tampon strip prior to its being rolled to form the FIG. 1 tampon.

FIG. 4 is a view of a tampon strip prior to its being rolled to form the FIG. 2 tampon.

FIGS. 5, 6 and 7 each illustrate different modes for attaching the cavity generating string and the pull string to the strip.

FIG. 8 is an end elevational view of the insert end of the FIGS. 1 and 2 tampons.

FIG. 9 is an axial sectional view of the FIG. 2 tampon prior to "flowering".

FIG. 10 is an enlarged fragmentary axial sectional view of the "flowered" insert end of a tampon.

FIG. 11 is a schematic view showing the "flowered" tampon arranged within the vagina.

FIG. 12 is a similar view showing the tampon wetted and expanded.

FIG. 13 is an axial sectional view of the insert end of another form of tampon.

FIG. 14 is an enlarged axial sectional view of the tampon insert end shown in FIG. 13, after being expanded or "flowered".

FIG. 15 is a perspective view of a substantially rectangular shaped layer of fluid absorbent material used to form the tampon shown in FIG. 16.

FIG. 16 is a perspective view of the tampon referred to in the FIG. 15 description.

FIG. 17 is a perspective view of another embodiment of the invention.

FIG. 18 is a view of another form of tampon prior to being finally compressed.

FIG. 19 is a view of the tampon formed from the structure shown in FIG. 18.

FIG. 20 illustrates the preliminary formation of another form of tampon.

FIG. 21 is illustrative of the tampon formed from the FIG. 20 disclosure.

FIG. 22 shows the FIG. 21 tampon expanded at its insert end.

FIG. 23 is a further modification of the FIG. 21 tampon.

Referring now to the illustration of representative tampons embodying features of the invention and shown particularly in FIGS. 1 through 12 of the accompanying drawings, the tampon 11 (FIG. 1) is fabricated from a strip 12 (FIG. 3) of cotton or equivalent moisture absorbent material, whereas the tampon 13 (FIG. 2) is fabricated from a strip 14 (FIG. 4) of like material. Specifically, the strips 12, 14 each have an end portion 15, 15a, respectively, that is of a length commensurate with the length of the tampon ultimately formed. These end portions 15, 15a may constitute a third or perhaps as much as one-half of the length of the respective strips 12, 14, and they are folded over onto the adjacent portion of the respective strips 12, 14 to provide a double thickness of material. A string is then stitched, as shown at 16, across the width of the folded area, inwardly of the fold, in a manner to leave a free end string portion 17 extending downwardly therefrom. The folded area of the FIGS. 3 and 4 disclosures, also has a second string stitched to one-half of the folded area, as at 18, with the free end portion 18a of the string extending upwardly beyond the upper edge of the strip.

The strip 12 is of uniform width so that the tampon 11 is formed by rolling the strip substantially cylindrical; whereas the strip 14, which has an inclined bottom edge 19, when rolled, produces a frusto-conical tampon 13; that is, one that increases in diameter as it's insert end is approached. This frusto-conical shape is much to be desired from the standpoint of a proper self-adjusting fit in the vagina 21 which is of reduced diameter at the entrance end. Thus, when the frusto-conical tampon is in place in the vagina (FIG. 11) it conforms substantially to the shape of the vagina, and is thereby more easily retained in place, especially after absorbing moisture ans swelling, as shown in FIG. 12.

The protruding string portion 17 constitutes means to be grasped for pulling the tampon from the vagina. The other protruding string 18a constitutes an instrument to expand the insert end of the tampon radially. Such expansion, effected by grasping the string portion 18a and carrying it into a radial position (FIG. 8) and then rotating it circumferentially, results in the creation of a deep cavity or recess 22 (FIG. 10) on the insert end of the tampon. Such a deep cavity is most desired when it becomes necessary to apply medication to the vagina and/or cervix. It tends to retain the medication is position within the vagina.

In the prior application referred to hereinabove, the string portion comparable to the string 18a is stitched to the tampon strip over the entire width of the strip with the result that but a very shallow cavity can be generated, and only after considerable manipulation to effect lossening of the tampon material sufficiently to permit its spreading outwardly radially. However, because of the frequent need for the application of large amounts of medication, the herein disclosed improved structure affords the creation, with minimum effort, of a relatively deep wide flaring cavity 22 having maximum capacity.

The tampons described may be inserted and withdrawn by the user. However, should medication or the like be indicated or required, the expanded tampon structure can be and preferably is placed in the vagina by a physician or gynecologist using a vaginal speculum and a good light.

FIGS. 5, 6 and 7 each illustrate different attachments for the string on the insert end of either the FIG. 1 or FIG. 2 tampon. In FIG. 5 the string 18b is stitched, as at 18c, to the upper half of the folded end portion of the strip. In the FIG. 6 disclosure, the string 18d is secured midway between the edges of the strip by but one or two stitches 18e, and in FIG. 7, both the pull string 17a and the expansion string 18f are secured to the strip by being looped therearound as shown at 17b and 18g.

FIGS. 13 and 14 disclose an axial sectional view of the upper or insert end of a modified form of tampon, whether cylindrical or frusto-conical. Here an axial recess 23 of considerable depth is formed in the insert end of the tampon. Before insertion of the tampon into the vagina, a stick 24 of a size and shape to fit the recess is inserted thereinto and rotated circularily while being urged outwardly radially so as to loosen the surrounding fibers of the tampon and expand the insert end outwardly radially, as shown in FIG. 14, after which the stick is removed and medication, if needed, is placed in the recessed tampon end and the tampon then inserted into the vagina.

The tampon illustrated in FIGS. 15, 16 embodies essentially the basic structure of a tampon commercially known as "Tampax", with the exception that cavity forming means in the form of a manipulation string 18h is secured substantially midway between the ends of a substantially rectangular piece 25 of fluid absorption material which is subsequently rolled and compacted to form tampon 26, having the string 18h projecting from the axial center thereof so as to be manipulatable to generate a deep wide cavity in the insert end.

FIG. 17 is representative of a tampon commercially known as "Kotex". It is fabricated from a rolled thickness of fluid absorbent material and has a pull string 17c attached to it's outside end by being looped through a radial aperture 27. The manipulatable string 18i is secured at one end to the tampon a considerable distance inwardly from the insert end to facilitate generation of a medication cavity.

FIGS. 18, 19, illustrate a tampon of the character commercially known as "Meds" or "pursettes" equipped with the novelly disclosed manipulatable string 18k. Specifically, this type of tampon is fabricated from a length of compressed fluid absorbent material folded midway between its ends to provide two tightly closed halves 28 with a pull string 17d looped over it's medial fold portion. The manipulatable string 18k is secured to one of the halves, as at 29, to afford the unsecured area of the closed tampon halves to be expanded upon circular rotation of string 18k to produce cavity 30.

FIGS. 20, 21, 22, disclose a tampon structure 31 responding generally to one known commercially as "Playtex". Here the tampon is formed from two or more layers 32 of moisture absorbent material (FIG. 20) which is drawn into a cup-shape and then tightly compressed into cylindrical form (FIG. 21). The usual pull string 17e extends from its external end and a manipulatable string 18m, both connected to the tampon at 33, normally lies in the axial center of the compressed tampon. Upon movement of string 18m circularily while urging it outwardly radially, a cavity 34 (FIG. 22) is generated in the insert end.

FIG. 23 discloses a structure similar to that shown in FIGS. 21–22 and like numerals identify corresponding parts. Here the bottom or outer layer 35 of absorbent material is substantially smaller than the inner layer 36 so that the compressed tampon will have a single thickness wall at its insert end which is expandable upon manipulation of string 18n.

When the tampons illustrated become wetted they will swell up and expand to substantially occupy the vaginal canal as shown for example in FIG. 12. However, because of the frustro-conical shape of some of the disclosed tampons, such tampons will not slip out readily before becoming wetted, but may be withdrawn after wetting and swelling, without scratching or otherwise causing herniation of the vaginal mucosa and much discomfort.

Although I have described preferred embodiments of the invention, in considerable detail, it will be understood that the description thereof is intended to be illustrative, as details of the structure may be modified or changed without departing from the spirit or scope of the invention. Accordingly, I do not desire to be restricted to the exact construction and method shown and described.

I claim:

1. A tampon of the character described, comprising a generally cylindrical body made up of highly fluid absorbent material having an insert end and an outer end, a pull string extending from the outer end of said body, and a manipulatable string attached to the body a substantial distance inwardly from the insert end and extending axially beyond the insert end manipulatable for generating an axial recess in the said insert end of the body.

2. A tampon of the character described, comprising a generally cylinderical body made up of a strip of highly fluid absorbent material having its innermost end folded over upon itself, said body having an outer end and an insert end, a pull string secured to the folded end of the strip and extending beyond the outer end of said body, and a manipulatable string stitched to the said folded end of the strip along not more than one-half of the width of the strip and closely adjacent to the pull string.

3. A tampon of the character described comprising a generally cylinderical body made up of a strip of highly fluid absorbent material having its innermost end folded over upon itself, said body having an outer end and an insert end, a pull string secured to the folded end of the strip and extending beyond the outer end of said body, and a manipulatable string spot stitched to the strip at a point substantially midway between its edges and closely adjacent to the pull string securement.

4. A tampon of the character described comprising at least one layer of highly fluid absorbent material, a pull string and cavity forming means centrally secured to the layer, the pull string extending outwardly from one face of the material, the cavity forming means extending from the other face of the material, and said layer being folded cup-shaped and compressed to form a cylindrical body to substantially embrace the cavity forming means.

5. A tampon of the character described comprising a flat body composed of one or more layers of highly moisture absorbent material, a pull string connected to said layer substantially at the center thereof and extending from one side thereof, cavity forming means connected to said layer inwardly of an edge thereof and extending from said edge, said layer being folded over upon itself into substantially a cup-shaped form and compressed to substantially enclose the cavity forming means.

6. A tampon of the character described comprising a generally cylindrical body made up of a highly fluid absorbent material having a flat insert end and an outer end, wherein said fluid absorbent material constitutes a strip having one of its ends folded over upon itself, said strip being rolled upon itself with the folded over end innermost, a string attached to the folded innermost end to extend axially from the axial center of the body beyond both ends thereby to form beyond the outer end a pull string and beyond the insert end a manipulatable member for generating a conical recess in the flat end of the body, the attachment of the string to the folded portion permitting generation of said recess without moving the string axially through the body.

7. A tampon of the character described comprising a generally cylindrical body made up of a rolled elongated strip of highly fluid absorbent material with a folded over inner end, said tampon having an insert end and an outer end, a string extending axially through the body and secured to said folded over inner end to hold the string axially within the body between its ends, one end of said string extending beyond the outer end and constituting a pull string, and the other end of said string extending beyond the insert end far enough to constitute means manually manipulatable to generate an axially disposed concave recess in said insert end.

8. A tampon of the character described comprising a generally cylindrical body of highly fluid absorbent material, said body having an insert end and an outer end, a pull string extending axially from the outer end of said body, a string extending outwardly from the axial center of the insert end of said body, said strings being secured to the body along its axis, and the string on the insert end being extended far enough beyond the body to be manipulated against the secured axial position to generate a substantially conical axially disposed recess in said end.

* * * * *